(12) United States Patent
Siess et al.

(10) Patent No.: US 11,103,689 B2
(45) Date of Patent: *Aug. 31, 2021

(54) BLOOD PUMP

(71) Applicant: Abiomed Europe GmbH, Aachen (DE)

(72) Inventors: Thorsten Siess, Aachen (DE); Walid Aboulhosn, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 153 days.

This patent is subject to a terminal disclaimer.

(21) Appl. No.: 15/556,639

(22) PCT Filed: Mar. 16, 2016

(86) PCT No.: PCT/EP2016/055641
§ 371 (c)(1),
(2) Date: Sep. 8, 2017

(87) PCT Pub. No.: WO2016/146659
PCT Pub. Date: Sep. 22, 2016

(65) Prior Publication Data
US 2018/0050139 A1 Feb. 22, 2018

(30) Foreign Application Priority Data
Mar. 18, 2015 (EP) .................................... 15159676

(51) Int. Cl.
*A61M 60/205* (2021.01)
*A61M 60/414* (2021.01)
(Continued)

(52) U.S. Cl.
CPC ........ *A61M 60/205* (2021.01); *A61M 60/135* (2021.01); *A61M 60/50* (2021.01);
(Continued)

(58) Field of Classification Search
CPC ........ A61M 1/10; A61M 1/12; A61M 1/1086; A61M 1/1017; A61M 1/101; A61M 1/125;
(Continued)

(56) References Cited

U.S. PATENT DOCUMENTS 5,049,134 A * 9/1991 Golding .................... F04D 1/04
415/900
5,399,074 A 3/1995 Nose et al.
(Continued)

FOREIGN PATENT DOCUMENTS

JP H0678995 A 3/1994
JP 2003501155 A 1/2003
(Continued)

OTHER PUBLICATIONS

Office Action corresponding to Japanese Pat. Appl. No. 2017-549270 dated Nov. 19, 2019 (19 pages).
(Continued)

*Primary Examiner* — Jon Eric C Morales
(74) *Attorney, Agent, or Firm* — Botos Churchill IP Law LLP (57) ABSTRACT

A blood pump (1) comprises a pump casing (2) having a blood flow inlet (5) and a blood flow outlet (6) connected by a passage (7), and an impeller (3) arranged in said pump casing (2) so as to be rotatable about an axis of rotation (9). The impeller (2) is provided with blades (4) sized and shaped for conveying blood along the passage (7) from the blood flow inlet (5) to the blood flow outlet (6), the impeller (3) being rotatably supported in the pump casing (2) by at least one bearing (10, 20). A surface of the impeller (3) faces a surface of the pump casing (2) spaced from said surface of the impeller (3) by a clearance (31), the clearance (31) being in fluid connection with the passage (7) at a clearance
(Continued)

transition point (36). In order to wash out the clearance, at least one wash out channel (30) extends through the impeller (3) and is in fluid connection with the passage (7) via a first opening (34) and with the clearance (31) via a second opening (35). The first opening (34) of the wash out channel (30) is arranged in an area of the impeller (3) that—during operation of the blood pump (1)—is under a higher pressure than the clearance transition point (36) so as to cause a blood flow from the first opening (34) through the wash out channel (30) and the clearance (31) to the clearance transition point (36).

21 Claims, 9 Drawing Sheets

(51) Int. Cl.
| | |
|---|---|
| *A61M 60/50* | (2021.01) |
| *A61M 60/135* | (2021.01) |
| *A61M 60/824* | (2021.01) |
| *A61M 1/10* | (2006.01) |
| *A61M 60/82* | (2021.01) |
| *A61M 60/148* | (2021.01) |
| *A61M 60/818* | (2021.01) |

(52) U.S. Cl.
CPC ......... *A61M 60/824* (2021.01); *A61M 60/148* (2021.01); *A61M 60/414* (2021.01); *A61M 60/818* (2021.01); *A61M 60/82* (2021.01); *A61M 2205/3334* (2013.01)

(58) Field of Classification Search
CPC ........ A61M 2205/3334; A61M 1/1013; A61M 1/1015; A61M 1/1034; A61M 1/122; A61M 1/1012
USPC ..................................... 604/151; 600/16, 17
See application file for complete search history.

(56) References Cited

U.S. PATENT DOCUMENTS

| | | |
|---|---|---|
| 6,048,363 A | 4/2000 | Nagyszalanczy et al. |
| 6,527,699 B1 * | 3/2003 | Goldowsky ............. A61M 1/12 600/16 |
| 10,773,002 B2 * | 9/2020 | Siess ...................... A61M 1/101 |

FOREIGN PATENT DOCUMENTS

| | | |
|---|---|---|
| JP | 2013053591 A | 3/2013 |
| WO | WO-9409274 | 4/1994 |
| WO | 00/74748 A1 | 12/2000 |
| WO | WO-2013185073 | 12/2013 |

OTHER PUBLICATIONS

Office Action corresponding to Japanese Pat. Appl. No. 2017-549270 dated Jul. 28, 2020 (14 pages).

* cited by examiner

BLOOD PUMP

CROSS-REFERENCE TO RELATED APPLICATIONS

This application is a United States National Stage filing under 35 U.S.C. § 371 of International Application No. PCT/EP2016/055641, filed Mar. 16, 2016, which claims the benefit of European Patent Application No. 15159676.4, filed Mar. 18, 2015, the contents of all of which are incorporated by reference herein in their entirety. International Application No. PCT/EP2016/055641 was published under PCT Article 21(2) in English.

BACKGROUND

This invention relates to blood pumps to be implanted in a patient for supporting the patient's heart. In particular, the blood pump may be used as a "bridge to recovery" device, whereby the blood pump temporarily supports the patient's heart until it has sufficiently recovered.

Blood pumps of different types are known, such as axial blood pumps, centrifugal blood pumps or mixed type blood pumps, where the blood flow is caused by both axial and radial forces. Blood pumps may be inserted into a patient's vessel such as the aorta by means of a catheter, or may be placed in the thoracic cavity. A blood pump typically comprises a pump casing having a blood flow inlet and a blood flow outlet connected by a passage. In order to cause a blood flow along the passage from the blood flow inlet to the blood flow outlet an impeller is rotatably supported within the pump casing, with the impeller being provided with blades for conveying blood.

The impeller is supported within the pump casing by means of at least one bearing, which may be of different types depending on the intended use of the blood pump, for instance whether the blood pump is intended only for short term use (some hours or some days) or long term use (weeks or years). A variety of bearings are known, such as contact-type bearings and non-contact bearings. In non-contact bearings the bearing surfaces do not contact each other, e.g. in magnetic bearings, in which the bearing surface "levitate" due to repelling magnetic forces. Generally, contact-type bearings may include all types of bearings, in which the bearing surfaces may contact at least partially during operation of the pump at any time (i.e. always or intermittently), e.g. in slide bearings, pivot bearings, hydrodynamic bearings, hydrostatic bearings, ball bearings etc. or any combination thereof. In particular, contact-type bearings may be "blood immersed bearings", where the bearing surfaces have blood contact. Contact-type bearings may heat up during use and are subject to mechanical wear caused by the contact of the rotating bearing surface and the static bearing surface during operating of the pump. It is desirable to supply a cooling fluid to the bearing, such as the blood itself. In non-contact-type bearings, the bearing surfaces do not have physical contact but are spaced by a clearance, which is in fluid connection with the passage or other fluid supply. Likewise, other clearances between the impeller and the pump casing should be washed out to avoid blood clotting and clogging, for instance at the downstream front face of the impeller.

Arrangements for rinsing clearances or bearing surfaces within a blood pump are disclosed for instance in US 2011/0238172 A1. Wash out channels extend through the impeller and are in fluid communication with the passage and the clearance via first and second openings. The pressure distribution in the pump casing, where the pressure increases along the impeller in a downstream direction gives rise to a blood flow through the clearance and the wash out channel, the blood entering the clearance at a downstream end of the impeller and flowing through the wash out channel towards an area of the passage with lower pressure. This wash out flow has the disadvantage of depending on the rotational speed of the impeller, because a pressure difference must be created to cause the blood flow. Other forces such as centrifugal forces and a counter force due to the backward direction of the wash out flow also have to be overcome. In another embodiment disclosed in US 2011/0238172 A1, in which the impeller is supported in the pump casing by a hydrodynamic bearing, the inlet opening of the wash out channel is disposed at the upstream end of the impeller. Secondary blades at the downstream end of the impeller are provided to cause a wash out flow through the wash out channel and the clearance in a direction from an area of low pressure to an area of higher pressure.

SUMMARY OF THE INVENTION

It is therefore a primary object of the present invention to provide a blood pump wherein blood flow stagnation and blood clotting and clogging in clearances between rotating parts and static parts of the blood pump, in particular between the static and rotating parts of the bearing or the impeller and the pump casing, are effectively avoided, in particular independently of the rotational speed or operating conditions of the pump. It is a further object of the present invention to provide a blood pump wherein clearances can be effectively washed out. It is still a further object of the present invention to provide a blood pump that allows for effective cooling of a contact-type bearing.

The primary object is achieved according to the present invention by a blood pump with the features of independent claim 1. Preferred embodiments and further developments of the invention are specified in the claims dependent thereon.

Like known blood pumps, the blood pump according to the invention comprises a pump casing having a blood flow inlet and a blood flow outlet connected by a passage. The pump casing may be understood as comprising all static parts of the blood pump. An impeller or rotor is arranged in said pump casing so as to be rotatable about an axis of rotation, which may be the longitudinal axis of the impeller, with the impeller being provided with blades sized and shaped for conveying blood along the passage from the blood flow inlet to the blood flow outlet. At least one bearing is provided to rotatably support the impeller. A surface of the impeller faces a surface of the pump casing spaced from said surface of the impeller by a clearance, wherein the clearance is in fluid connection with the passage at a clearance transition point. In order to enable the clearance to be washed out, at least one wash out channel extends through the impeller and is in fluid connection with the passage via a first opening and with the clearance via a second opening.

In contrast to known blood pumps, the first opening of the wash out channel is arranged in an area of the impeller that—during operation of the pump—is under a higher pressure than the clearance transition point so as to cause a blood flow from the first opening through the wash out channel and the clearance to the clearance transition point. In other words, the wash out flow is directed in a "forward" direction, that is to say, in a direction towards the blood flow outlet of the pump casing, because the first opening of the wash out channel, i.e. an inlet opening of the wash out channel, is in a high pressure area of the impeller, while the clearance transition point is e.g. at the downstream side of the impeller, where the pressure is lower. Thus, by utilizing this pressure difference, in particular the local pressure gradient within the wash out channel, that occurs during operation of the blood pump, a forward flow wash out is created. This has the advantage that the necessary pressure difference is present at any time during operation of the pump, independent of the rotational speed and operating condition (e.g. preload, afterload, magnitude of primary forward flow), in particular also at a beginning of operation, when the rotation of the impeller starts and the rotational speed is low, in particular below the design speed of the blood pump. In contrast, in known blood pumps, where the wash out flow is directed in a "backward" direction, a pressure difference has to be built up, which takes some time during which the wash out flow is slow or may stagnate. This may lead to blood clotting and clogging in the clearance or the wash out channel or both. Furthermore, a backward flow has to overcome forces caused by the main direction of flow, which may also lead to stagnation of the wash out flow and consequently blood clotting and clogging. According to the present invention, a wash out flow is present in a "forward" direction throughout the time of operation of the blood pump, in particular utilizing the pressure distribution within the pump casing during operation of the pump. This flow may be further increased by a secondary pump as described in more detail below. It will be appreciated, however, that such secondary pump is not necessary for the functionality of the present invention.

In a preferred embodiment, the first opening of the wash out channel may be disposed in a downstream half of the impeller. During operation of the pump, the pressure increases along the length of the impeller, in particular in a region where the blades of the impeller are disposed. Therefore, in the downstream half of the impeller, a higher pressure is present than in the upstream half of the impeller. Since, according to the invention, a high pressure at the first opening of the wash out channel is needed, more specifically a higher pressure than at the clearance transition point, it is preferable to place the first opening in the downstream half of the impeller. More preferably, the first opening may be placed in a downstream third, a downstream quarter or a downstream fifth of the impeller. In particular, it is advantageous to place the first opening as close as possible to the downstream end of the impeller, for instance within the last 10 percent of the length of the impeller in the downstream direction.

In terms of the pressure distribution, the first opening of the wash out channel preferably is disposed in an area of the impeller where—during operation of the pump—the pressure is higher than a median pressure with respect to a pressure distribution along a length of the passage where the impeller is situated, more preferably where the pressure is substantially the maximum pressure. A high pressure difference between the first opening of the wash out channel and the clearance transition point improves the wash out flow from the first opening of the wash out channel to the clearance transition point.

In order to further improve the wash out flow, the blades may be specifically shaped to support the aforementioned pressure distribution within the pump, in particular to create a high pressure at the first opening of the wash out channel. The wash out flow may be further improved by providing a secondary pump that is operatively associated with the wash out channel for pumping blood through the wash out channel towards the clearance transition point. The secondary pump may be formed at least partially by said at least one wash out channel in that the wash out channel extends through the impeller along a direction having at least one tangential directional component. In other words, the second pump may be particularly formed at least partially by said at least one wash out channel itself which may be sized, shaped and arranged so as to pump blood through the wash out channel towards the bearing. The wash out flow may then be denoted as active wash out flow.

The active wash out flow is particularly useful for cooling a contact-type bearing or a "blood immersed bearing", since the amount of blood that is delivered to the bearing to wash out and cool the bearing is increased compared to a pump without a secondary pump. Cooling of the bearing can be further improved by effectively dissipating the heat from the bearing surfaces. For this purpose, the bearing may comprise a highly conductive material, such as stainless steel, that can dissipate the heat better than e.g. ceramics or titanium. It may be advantageous to provide a bearing with at least two components, in particular where the bearing surface is made of a smooth and resistant material, such as ceramics, e.g. provided in the form of a ceramic cap, while a portion of the bearing facing away from the bearing surface may be made of a highly conductive material, such as stainless steel.

In one embodiment, the wash out channel may extend linearly through the impeller and be offset relative to the axis of rotation. In particular, the wash out channel may extend in a plane that is parallel to the axis of rotation. By providing an arrangement having linear wash out channels that are skew with respect to the axis of rotation, i.e. do not intersect the axis of rotation, it is possible to cause an active wash out flow through the wash out channel.

In another embodiment, the wash out channel may be curved and extend from the first opening in a direction around the axis of rotation, in particular along a spiral shape. A spiral shape is to be understood as any curved, spiral, helical or otherwise curved shape in a direction about the axis of rotation at any length. Such shape is advantageous because it may support an active wash out flow.

Preferably, the wash out channel extends from the first opening at an angle relative to a surface of the impeller in a circumferential direction opposite the direction of rotation. In particular in contrast to a wash channel that extends perpendicularly to the surface of the impeller, an angled inlet opening facilitates the entrance of blood into the wash out channel and increases the flow rate through the wash out channel. This effect may be further improved by choosing an appropriate angle. For instance, the angle may be less than 20°, preferably less than 15°, more preferably less than 10°. The wash out channel may extend from the first opening in a substantially tangential direction relative to a surface of the impeller, in other words at a very small angle with respect to the surface of the impeller. It is important, however, that the angle is in a circumferential direction opposite the direction of rotation, in other words that the first opening opens in the direction of rotation to increase the amount of blood that flows through the wash out channel compared to an arrangement in which the wash out channel extends perpendicularly to the surface of the impeller.

In an embodiment, a distance between the second opening and the axis of rotation is less than or equal to a distance between the first opening and the axis of rotation. In other words, in a downstream direction, the wash out channel extends in a direction towards the axis of rotation. Preferably, in order to reduce the centrifugal forces that have to be overcome by the wash out flow within the wash out channel, a distance between the first opening and the axis of rotation is as small as possible. In other words, the distance between the first opening and the second opening in a radial inward direction should be as small as possible. It is further preferable if the distance between the axis of rotation and the first opening is significantly smaller than a distance between the axis of rotation and the clearance transition point, e.g. half (50%) or less than half, less than 40% or even less than 30%. This arrangement can be improved, i.e. the distance between the first opening and the clearance transition point can be increased, in centrifugal blood pumps compared to axial or mixed-type blood pump.

The impeller may comprise a central opening extending along the axis of rotation and accommodating the bearing, with the second opening being in fluid connection with the central opening. Furthermore, the wash out channel may be directed towards the axis of rotation substantially in a radial direction at the second opening. This may improve rinsing of the bearing and thereby cooling of the bearing.

Preferably, the first opening of the wash out channel is disposed adjacent to one of the blades of the impeller on a forward side of the blade with respect to the direction of rotation (generally referred to as the positive pressure side of the blade). In this area, the pressure is higher in particular compared to an area on a backward side of the blade (generally referred to as the negative pressure side of the blade), such that an active wash out flow through the wash out channel can be improved. In an embodiment, the first opening may be disposed on the forward side of the blade, while the second opening may be disposed on the backward side of the blade, that is to say both openings are disposed on a radially outer surface of the impeller and the wash out channel extends underneath and crosses the blade. In another embodiment, the wash out channel may extend within the blade, whereby the first opening is disposed on the forward side of the blade and the second opening is disposed in the blade, in particular on a radially outer edge of the blade. It is to be understood that the wash out channel is in fluid communication with the areas to be washed out.

As explained, the performance or output of the secondary pump can be improved by a specific arrangement of the wash out channel through the impeller, for instance a linear or curved wash out channel, which may extend at an angle relative to the surface of the impeller. The performance of the secondary pump may be further improved by the cross section of the first opening of the wash out channel. The cross section of the first opening may be circular or non-circular. In case the wash out channel has a circular cross section and extends at an angle relative to the surface of the impeller, this will result in a non-circular cross-section, such as an elliptical cross-section. In an embodiment, the first opening may be formed by an end portion of the wash out channel that is at least partially exposed due to an incline of the wash out channel relative to a surface of the impeller. In other words, the first opening may be elongate on the surface of the impeller, which may further increase the amount of blood that enters the wash out channel during operation of the blood pump.

In another embodiment, a protrusion may extend into the first opening of the wash out channel, being sized and shaped to increase a blood flow through the first opening into the wash out channel, in particular compared to a cross section of the first opening without the protrusion. The shape of the first opening without the protrusion may be either circular or non-circular. The protrusion may be disposed on a backward side of the first opening relative to the direction of rotation such that it acts as an "airfoil" to promote inflow of blood into the first opening and thereby improve performance of the secondary pump. Alternatively or additionally, the impeller may comprise a wing extending radially therefrom and being disposed adjacent to and behind the first opening of the wash out channel with respect to the direction of rotation. Preferably, the wing extends over the first opening of the wash out channel and opens in the direction of rotation so as to allow blood to enter the first opening. The wing forms a pocket that collects blood during rotation of the impeller and directs the collected blood into the first opening. In order to achieve a similar effect, the impeller may comprise a nose or protrusion comprising the first opening such that the cross section of the first opening extends at an angle relative to the surface of the impeller, preferably an angle greater than 45°, more preferably an angle of 90°, and opens in the direction of rotation. This may significantly increase the amount of blood that flows into the wash out channel.

Preferably, the blood pump comprises two or more of the above described wash out channels which may be symmetrically arranged with respect to the axis of rotation. In particular, the blood pump may comprise two, three, four, five or six wash out channels.

In addition to the size, shape and arrangement of the wash out channels forming at least part of the secondary pump, the secondary pump may further comprise grooves or blades formed in a surface of the impeller. Such secondary grooves or blades may be disposed at a downstream front face of the impeller to support the blood flow through the wash out channel towards the bearing.

In an embodiment, the impeller may have a portion in a downstream direction extending radially outward, the first opening of the wash out channel being disposed in said portion. In particular, said portion conically tapers radially outward in a downstream direction. The portion may be integrally formed with the impeller or separately formed. The performance of the secondary pump may be further increased by arranging the first opening in a radially extending portion of the impeller such that it is directed in a direction opposite the main direction of the blood flow through the passage. The first opening may then catch more blood and improve the performance of the secondary pump. The blades of the impeller may extend over said portion.

BRIEF DESCRIPTION OF THE DRAWINGS

The foregoing summary, as well as the following detailed description of preferred embodiments, will be better understood when read in conjunction with the appended drawings. For the purpose of illustrating the present disclosure, reference is made to the drawings. The scope of the disclosure is not limited, however, to the specific embodiments disclosed in the drawings. In the drawings.

DETAILED DESCRIPTION

Figure 1:
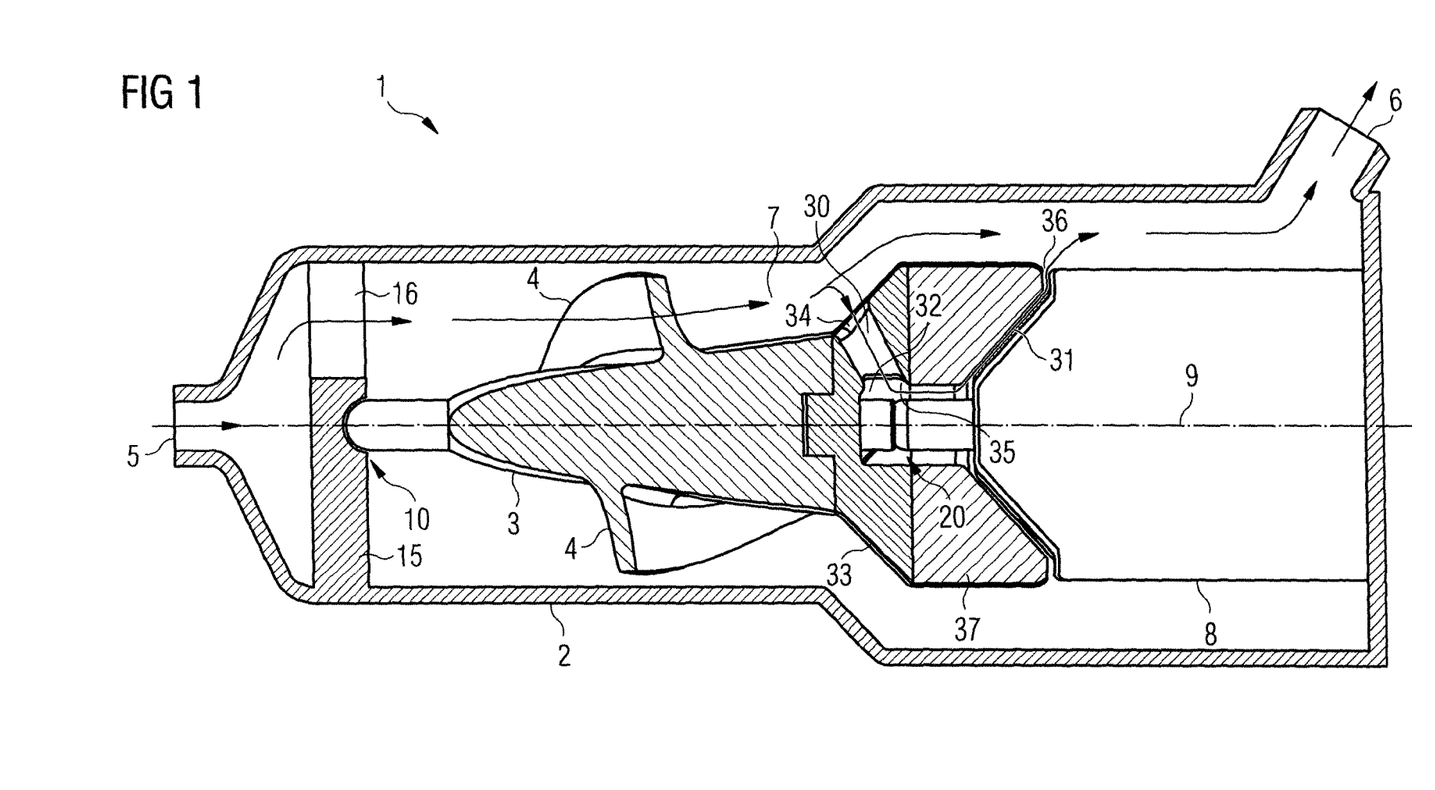
FIG. 1 and FIG. 1A show a cross sectional view of a blood pump according to the invention for extracardiac use.
Figure 2:
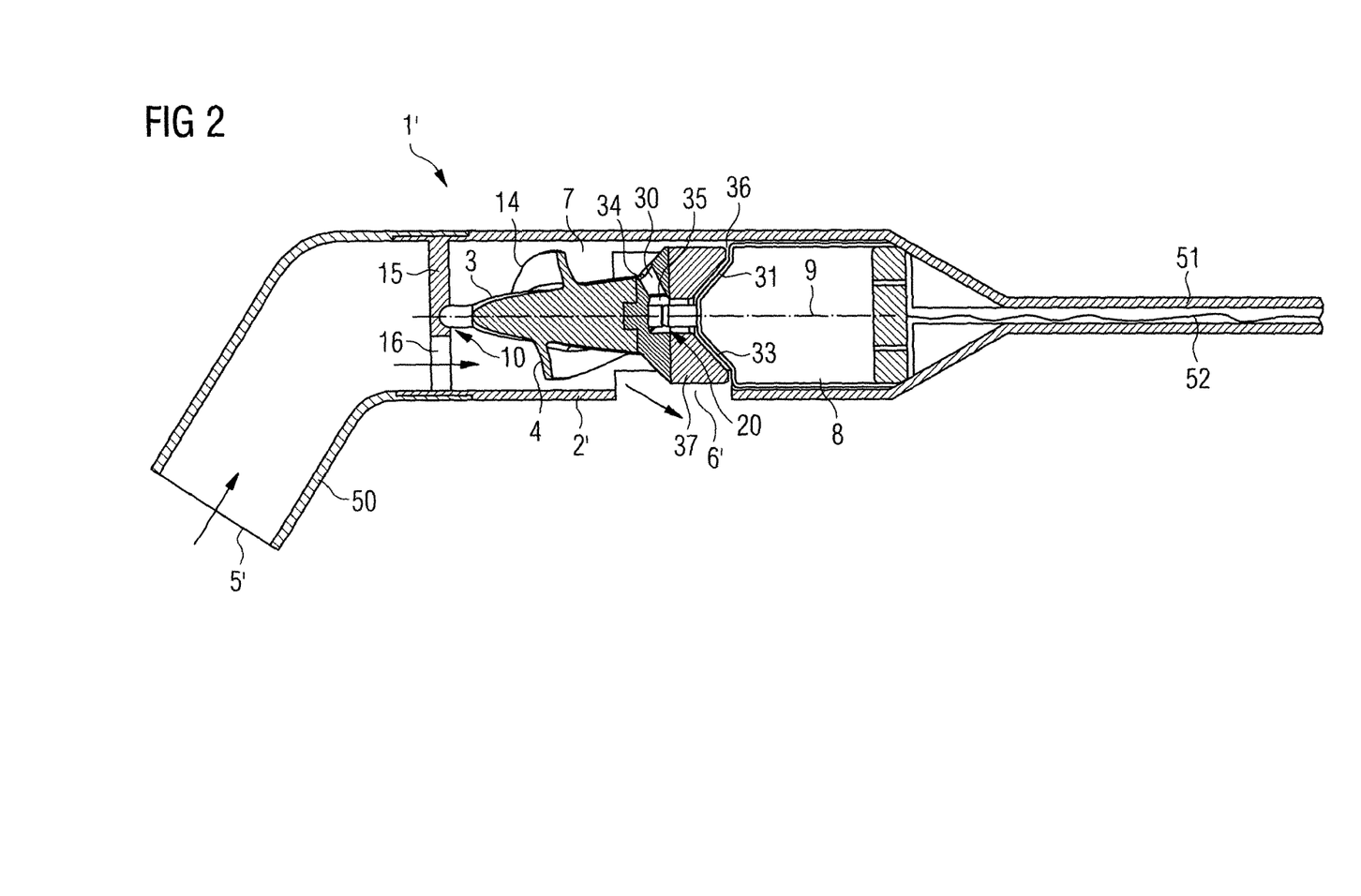
FIG. 2 shows a cross sectional view of a blood pump according to the invention designed as a catheter pump.

Referring to FIG. 1, a cross sectional view of a blood pump 1 is illustrated. The blood pump 1 is designed for extracorporeal, extracardiac or extraluminal use and comprises a pump casing 2 with a blood flow inlet 5 and a blood flow outlet 6. During operation, the pump casing 2 is placed outside a patient's body and the blood flow inlet 5 and the blood flow outlet 6 are connected to respective connectors (in particular inflow from the heart and outflow to the aorta). FIG. 2 shows an embodiment that is similar to that of FIG. 1 with the difference that it is designed as a catheter pump 1'. The blood flow inlet 5' is at the end of a flexible cannula 50 which is placed through a heart valve, such as the aortic valve, during use, while the blood flow outlet 6' is placed in a side of the pump casing 2' and is placed in a heart vessel, such as the aorta. The blood pump 1' is connected to a catheter 51, and an electric wire 52 extends through the catheter 51 for driving the pump 1'. Both blood pumps 1 and 1' function in the same way. It will be appreciated that all features described below are applicable for both embodiments.

The blood is conveyed along a passage 7 connecting the blood flow inlet 5 and the blood flow outlet 6. An impeller 3 is provided for conveying blood along the passage 7 and is rotatably mounted about an axis of rotation 9 within the pump casing 2 by means of a first bearing 10 and a second bearing 20. The axis of rotation is preferably the longitudinal axis of the impeller 3. Both bearings 10, 20 are contact-type bearings. At least one of the bearings 10, 20, however, could be a non-contact-type bearing, such as a magnetic or hydrodynamic bearing. The second bearing 20 is a pivot bearing having spherical bearing surfaces that allow for rotational movement as well as pivoting movement to some degree. The first bearing 10 is disposed in a supporting member 15 to stabilize the rotation of the impeller 3, the supporting member 15 having at least one opening 16 for the blood flow. Blades 4 are provided on the impeller 3 for conveying blood once the impeller 3 rotates. Rotation of the impeller 3 is caused by an electric motor stator 8 magnetically coupled to an end portion 37 of the impeller 3. Other suitable driving mechanisms are possible as will be appreciated by a person skilled in the art. The illustrated blood pump 1 is a mixed-type blood pump, wherein the major direction of flow is axial. It will be appreciated that the blood pump 1 could also be a purely axial blood pump, depending on the arrangement of the impeller 3, in particular the blades 4.

The impeller 3 comprises a portion 33 that is disposed in a downstream portion of the impeller 3 and extends radially outwards. The portion 33 can be denoted as a yoke, flange portion or end portion. In this embodiment, the portion 33 comprises an outer surface that extends at an angle of 45° with respect to the axis of rotation 9. Other appropriate angles could be chosen, e.g. an angle between 30° and 60° or could be a curved surface. The portion 33 may be formed integrally with the impeller 3 or separately as shown in this embodiment. At least one wash out channel 30, preferably two or more, such as three, four, five or six wash out channels 30, only one of which is shown in FIG. 1, extends through the impeller 3, in particular through the portion 33, so as to allow for washing out or rinsing the pivot bearing 20 and the clearance 31 between the impeller 3 and a static part of the blood pump 1, in particular the pump casing 2 or the motor 8, which may be regarded as associated with the pump casing 2. The at least one wash out channel 30 may also extend at least partially into the main portion of the impeller 3 beyond the portion 33.

The wash out channel 30 has a first opening 34 or inlet opening and a second opening 35 or outlet opening. The first opening 34 forms a fluid connection between the passage 7 and the wash out channel 30, while the second opening 35 is in fluid connection with the clearance 31. In particular, the second opening 35 is in fluid connection with a central bore or central opening 32 of the portion 33 accommodating the second bearing 20. The clearance 31 is in fluid connection with the passage 7 via a clearance transition point 36, i.e. a location where the clearance 31 opens to the passage 7.

Figure 1A:
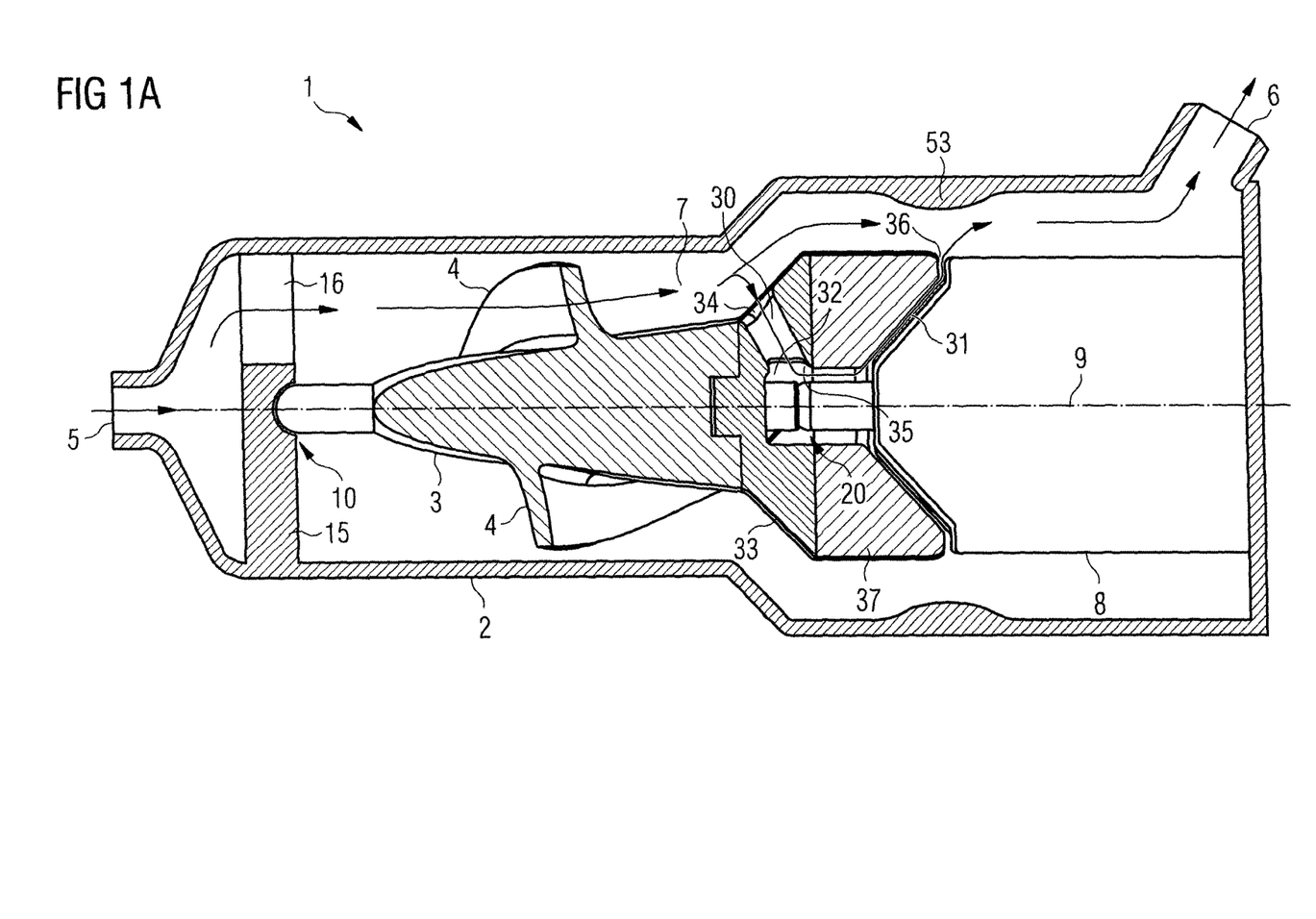

The first opening 34 of the wash out channel 30 is disposed in a downstream half of the impeller 3. In particular, the first opening 34 is disposed in an area of the impeller 3 that is under a high pressure caused by the rotation of the impeller 3 during operation of the blood pump 1. In particular, the first opening 34 may be in an area close to or at the maximum pressure within the pump casing 2. The pressure is increased by the blades 4 and by the deflection of fluid from an axial flow direction to a radial direction and then decreases downstream of the blades 4. Therefore, a pressure at the clearance transition point 36 is lower than at the first opening 34 of the wash out channel 30 due to an appropriate choice of the position of the first opening 34, which is near the downstream end of the impeller 3. This pressure distribution, which may be enhanced by choosing the shape of the blades 4 accordingly, results in a flow direction from the first opening 34 through the wash out channel 30 and the clearance 31 to the clearance transition point 36. Alternatively, a further drop in pressure at point 36 could be achieved by creating a local pressure drop by the Venturi effect in the proximity of point 36, e.g. by providing a narrowing 53 of the passage 7 (see FIG. 1A). In other words, blood flows through the wash out channel 30 in a forward direction towards the blood flow outlet 6 of the pump casing 2. Blood clotting can be effectively avoided at any time during operation of the blood pump 1, in particular also during phases with low rotational speed below the design speed of the blood pump 1, because the forward flow wash out occurs at any rotational speed.

Apart from washing out the pivot bearing 20 and the clearance 31, the blood flow through the wash out channel 30 provides cooling for the pivot bearing 20. The pivot bearing 20 is arranged in the central opening 32 of the portion 33. Thus, blood is conveyed through the wash out channel 30 towards the bearing 20. The pivot bearing 20 can be effectively cooled and rinsed. The effect can be further improved by providing a secondary pump that actively pumps blood through the wash out channel 30 towards the bearing 20 as will be described in detail below.

Figure 3:
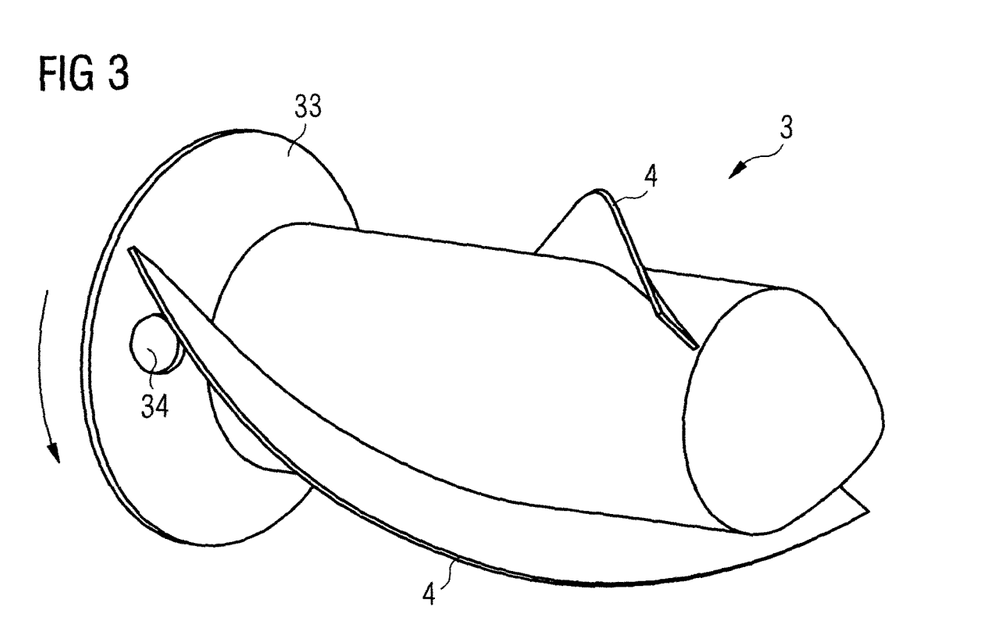
FIG. 3 shows a perspective view of an impeller.
Figure 4A:
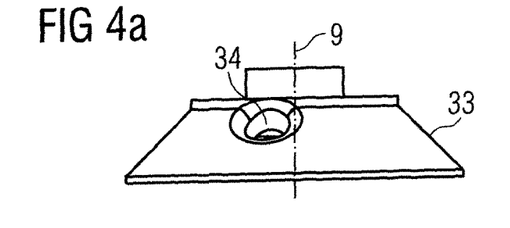
FIGS. 4a to 4d show different views of a portion of an impeller.
Figure 4B:
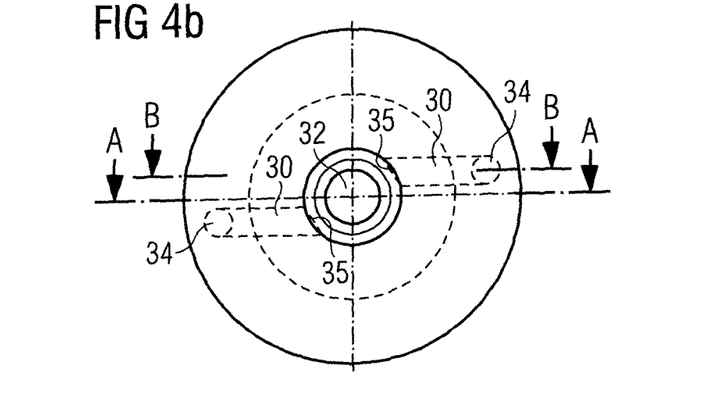
Figure 4C:
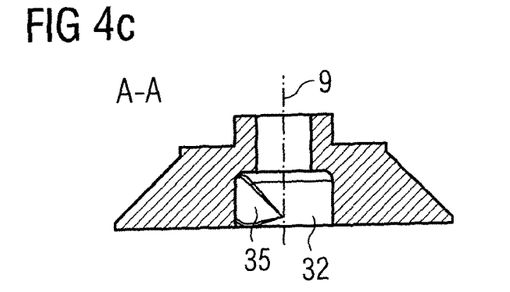
Figure 4D:
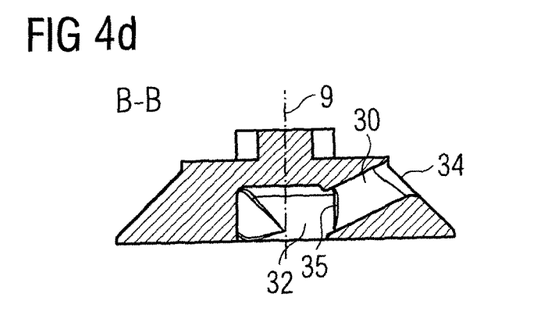

Now referring to FIG. 3, an embodiment of an impeller 3 is shown. The impeller has blades 4 arranged around a body of the impeller 3 and sized and shaped for conveying blood when the impeller 3 rotates in a direction of rotation (indicated by an arrow in FIG. 3). The impeller 3 has a portion 33 at its downstream end, wherein the portion 33 has at least one wash out channel 30 having an inlet opening 34. As explained above, the inlet opening 34 is arranged in an area of the impeller 3 that is under a high pressure to ensure that the blood flow through the wash out channel 30 is directed from the first opening 34 or inlet opening to the second opening 35. In this embodiment, the inlet opening 34 is disposed on a forward side of one of the blades 4 with respect to the direction of rotation (also referred to as the positive pressure side of the blade). In particular compared to a backward side of the blade 4 (also referred to as the negative pressure side of the blade), the pressure is higher on the forward side, which supports the direction of flow into the inlet opening 34 of the wash out channel 30. Nevertheless, the opening 34 may be disposed on the backward side of the blade 4, where the pressure may be sufficiently high because the opening 34 is disposed in the portion 33 at the downstream end of the impeller 3.

In FIGS. 4a-4d different views of an embodiment of the portion 33 are shown. In this embodiment, the wash out channels 30 form a secondary pump that pumps the blood through the wash out channels 30 from the respective first opening 34 to the second opening 35 and, thus, to the central opening 32 and the bearing 20 and further to the clearance transition point 36 (see FIG. 1). In this embodiment, the wash out channels 30 extend linearly through the impeller 3 and are offset with respect to the axis of rotation 9 (indicated by dashed lines in FIG. 4b, which is a bottom view of the portion 33). The wash out channels 30 extend in planes that are parallel to the axis of rotation 9, such that the wash out channels 30 extend along a direction that has a tangential component. This arrangement enforces the blood flow in the direction from the first opening 34 towards the second opening 35. Two wash out channels 30 are shown in this embodiment. It will be appreciated, however, that three, four or more wash out channel can likewise be provided, which may be symmetrically arranged around the axis of rotation 9. As can be seen particularly in FIG. 4d, which is a cross sectional view along line B-B in FIG. 4b, the wash out channels 30 are inclined in the downstream direction. The second openings 35, which are downstream relative to the first openings 34, are closer to the axis of rotation 9 than the first openings 34. The wash out channels 30 open to the central opening 32 which at least partially accommodates the second bearing 20 as shown in FIG. 1.

Figure 5A:
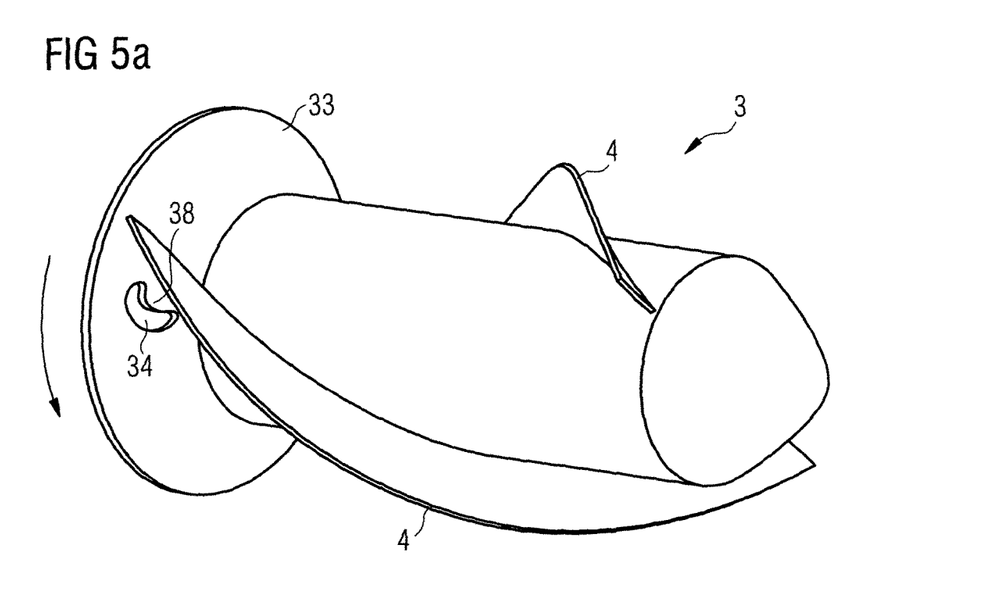
FIGS. 5a and 5b show other embodiments of an impeller.
Figure 5B:
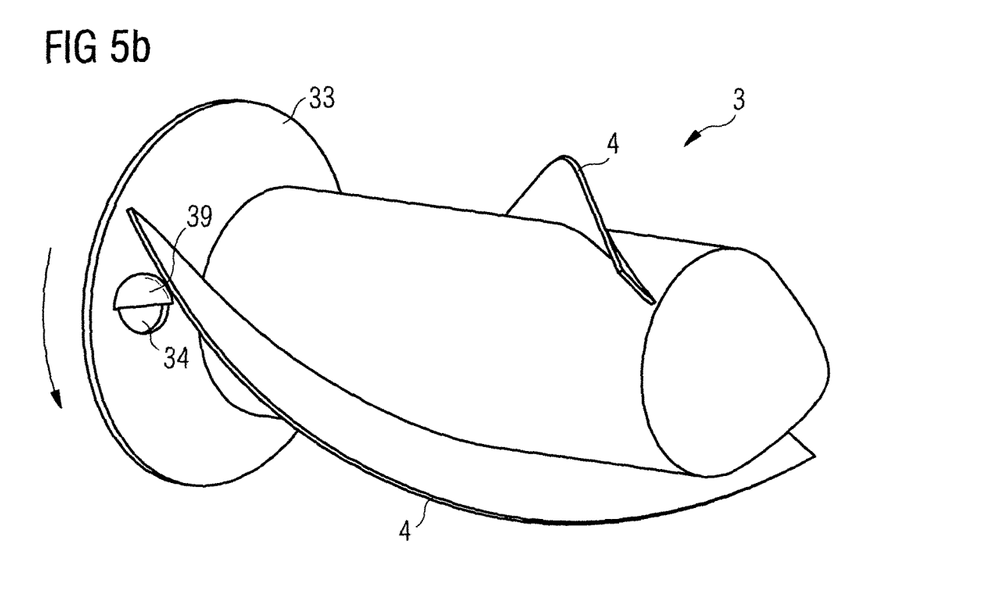

Further embodiments of an impeller 3 having wash out channels 30 that form a secondary pump are shown in FIGS. 5a and 5b. According to the embodiment of FIG. 5a, the first opening 34 is not circular. More precisely, a protrusion 38 extends into the first opening 34 for enhancing the amount of blood that flows through the first opening 34 into the wash out channel. The protrusion 38 is arranged at a backward side of the first opening 34 with respect to the direction of rotation. The resulting shape of the first opening 34 may be denoted as a kidney shape. It acts like an "airfoil" such that a pull or suction is created upon rotation of the impeller 3 to increase the amount of blood that enters the first opening 34, in particular compared to an embodiment without the protrusion 38 (such as the embodiment of FIG. 3). The shape of the protrusion 38 can be chosen according to the desired amount of blood that should flow through the wash out channels 30. The cross section of the first opening 34 may be symmetric or asymmetric.

Alternatively or in addition to the protrusion 38, a wing 39 can be provided as shown in FIG. 5b. The wing 39 is arranged behind the first opening 34 with respect to the direction of rotation and forms a pocket to catch a larger amount of blood upon rotation of the impeller 3 in the direction of rotation. The wing 39 may have any size and shape that is suitable to increase the amount of blood that enters the first opening 34 compared to an embodiment without the wing 39 (such as the embodiment of FIG. 3). The same effect can be achieved by arranging the first opening 34 in a nose or protrusion that extends radially from the impeller 3, with the first opening 34 pointing in the direction of rotation.

Figure 6A:
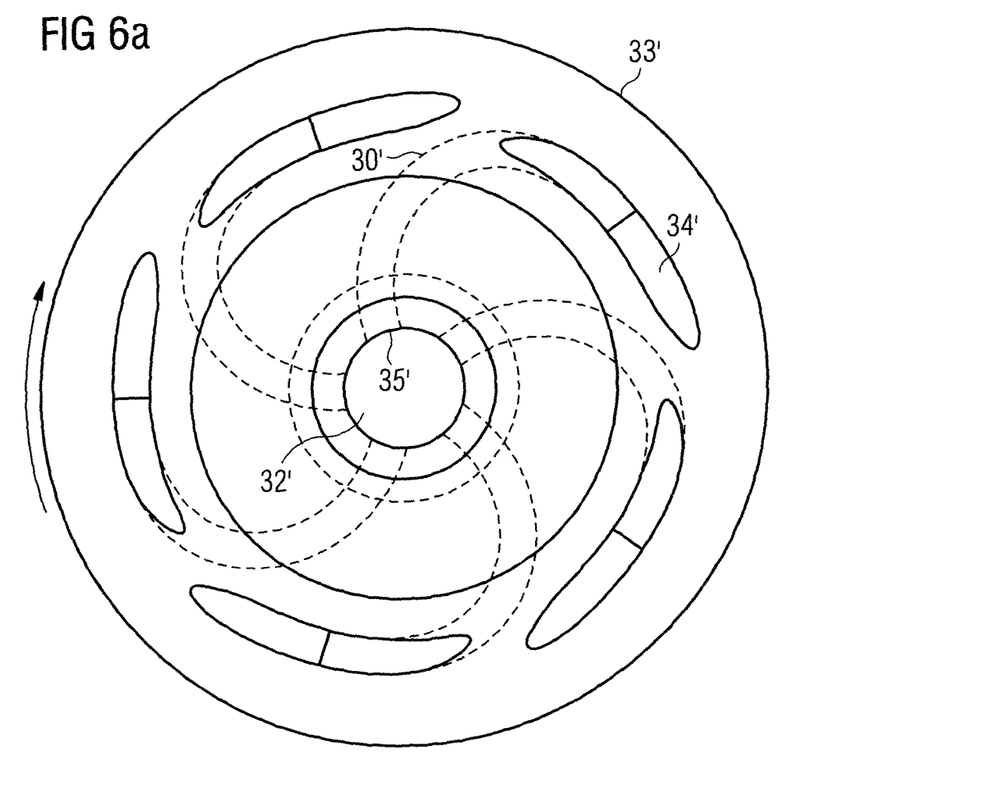
FIGS. 6a and 6b show other embodiments of a portion of an impeller.
Figure 6B:
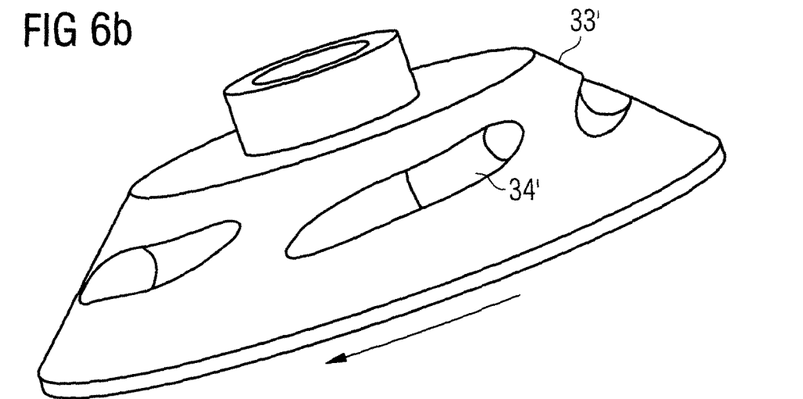

Referring now to FIGS. 6a and 6b, an embodiment of a portion 33' having wash out channels 30' is shown. The direction of rotation is indicated by an arrow. As in the above described embodiments, the wash out channels 30' have a first opening 34' and a second opening 35' facing a central opening 32'. The wash out channels 30' form part of a secondary pump as described in connection with the other embodiment to force a blood flow in a direction from the first openings 34' to the second openings 35' towards the second bearing 20. In this embodiment, the wash out channels 30' are curved and extend around the axis of rotation 9 in a spiral shape. It will be appreciated that the term "spiral shape" comprises any curved shape, whether it forms a regular spiral or any other curved shape having at least one tangential component. The wash out channels 30' enter the impeller 3 at the first opening at a small angle such that the first opening 34' is formed by an exposed portion of the wash out channel 30' and has an elongate shape. This promotes catching blood and helps to increase the amount of blood that enters the first opening 34', in particular compared to an arrangement in which the wash out channels 30 extend to the surface of the impeller 3 at a large angle, such as perpendicular or substantially perpendicular. The wash out channels 30' extend in a curved shape towards the central opening 32' and exit at the second openings 35' in a substantially radial direction. Blood is effectively pumped into the central opening 32' and thus to the second bearing 20, such that the second bearing 20 is rinsed and cooled. As explained in connection with FIG. 1, the blood flow through the wash out channels 30' effectively washes out the clearance 31 between the rotating impeller 3 and the static pump casing 2. In order to further improve the performance of the secondary pump, the secondary pump may further comprise grooves or blades formed on a surface of the impeller 3, in particular in the clearance 31.

It shall be understood that the secondary pump described above cannot overcome the centrifugal effect of a rotating channel of any shape that extends from a larger diameter to a smaller diameter without the assistance of the centrifugal pumping action at clearance 31.

Figure 7:
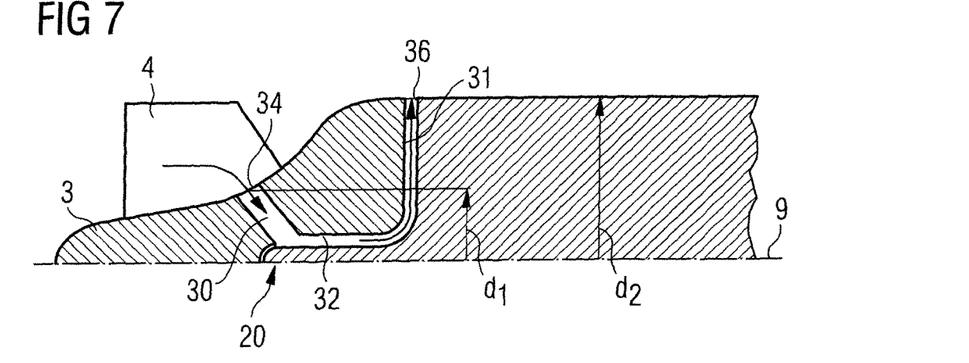
FIG. 7 shows a cross sectional view of a part of a blood pump according to another embodiment.

The performance of the secondary pump may be further improved by the position of at least one of the first opening 34 and the clearance transition point 36 relative to the rotational axis 9 and in particular relative to each other. As shown in FIG. 7 the first opening has a first distance $d_1$ to the rotational axis 9, while the clearance transition point 36 has a second distance $d_2$ to the rotational axis 9. The performance of the secondary pump can be improved if the first opening 34 is as close as possible to the rotational axis, that is to say if the distance $d_1$ is as small as possible and the wash out channel 30 extends only a little distance towards the rotational axis 9. This reduces centrifugal forces that have to be overcome by the wash out flow flowing in a direction towards the rotational axis. In particular, it is advantageous if the first distance $d_1$ is small compared to the second distance $d_2$, preferably $d_1$ may be half of $d_2$ or less.

Figure 8:
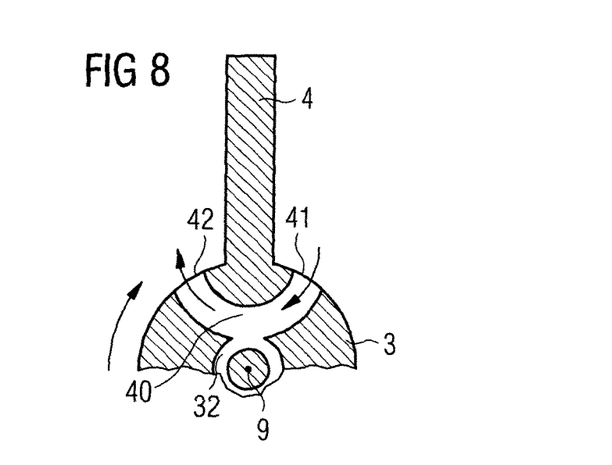
FIG. 8 shows a cross sectional view of a part of an impeller according to another embodiment.
Figure 9:
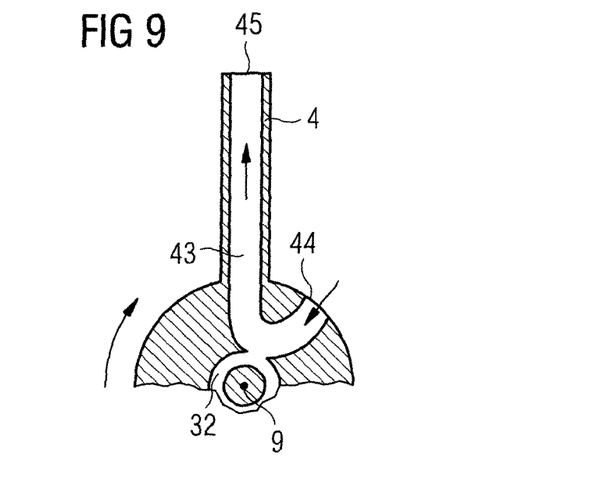
FIG. 9 shows a cross sectional view of a part of an impeller according to another embodiment.
Figure 10:
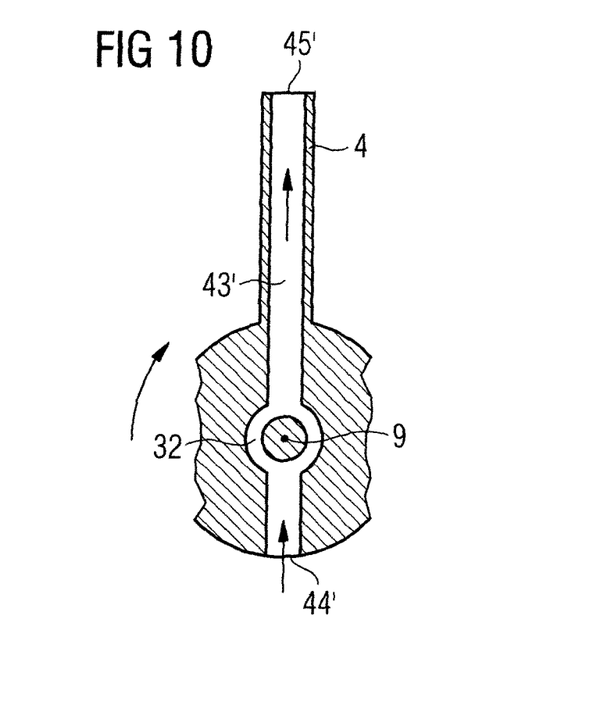
FIG. 10 shows a cross sectional view of a part of an impeller according to still another embodiment.

In another embodiment, shown in the cross section perpendicular to the rotational axis 9 in FIG. 8, the impeller 3 includes a wash out channel 40 with the first opening 41 and the second opening 42 being disposed on a radially outward surface of the impeller 3. The first opening 41 is disposed on a forward side of one of the blade 4 with respect to the direction of rotation (indicated by an arrow in FIG. 8), while the second opening 42 is disposed on a backward side of the blade 4. This causes a blood flow from the first opening 41 to the second opening 42. The wash out channel 40 is in fluid communication with the central opening 32 to wash out and cool the bearing 20. In the embodiment of FIG. 9, a wash out channel 43 is provided that has a first opening 44 disposed on a forward side of one of the blades 4 similar to the embodiment of FIG. 8. However, the wash out channel 43 extends through the blade 4 and exits at the second opening 45 which is arranged at an edge of the blade 4. This arrangement allows utilizing centrifugal forces to enforce a wash out flow from the first opening 44 to the second opening 45. FIG. 10 depicts another embodiment similar to that of FIG. 9. However, the first opening 44' of the wash out channel 43' is disposed diagonally opposite to the blade 4 through which the channel 43' extends and where the channel 43' exits at the second opening 45'. Thus, in this embodiment the wash out channel 43' runs diagonally or radially rather than tangential as in the embodiment of FIG. 9, such that it touches all sides of the bearing 20.

Figure 11:
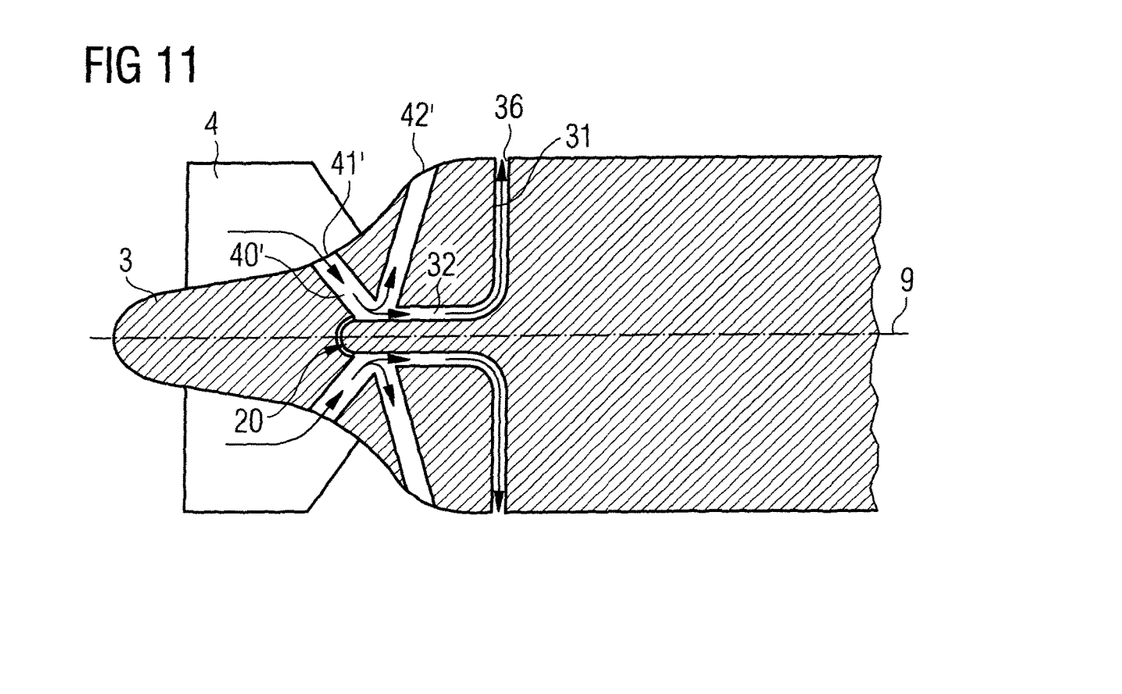
FIG. 11 shows a cross sectional view of a part of a blood pump according to another embodiment.

An embodiment similar to that of FIG. 8 is shown in FIG. 11. The wash out channel 40' has a first opening 41' disposed on a forward side of one of the blade 4 with respect to the direction of rotation, while the second opening 42' is disposed on a backward side of the blade 4 (please note that the wash out channel 40' is shown in the cross-sectional view of FIG. 11 although it does not extend in the plane of the cross section but rather similar to the cross-section shown in FIG. 8). The wash out channel 40' extends underneath the blade 4. However, in the embodiment of FIG. 11 the wash out channel 40' does not extend in one plane that is perpendicular to the longitudinal axis 9, but the second opening 42' is disposed downstream of the first opening 41'. Thus, the second opening 42' is also disposed radially outwards from the first opening 41'. The wash out flow can be increased by this arrangement by centrifugal forces in the exit section of the wash out channel 40' leading to the second opening 42'. Also the pressure difference in the passage 7 between the first opening 41' and second opening 42' enhances the wash out flow.

It will be appreciated that at least one of the wash out channels 40, 40', 43, 43' described in connection with FIGS. 8 to 11 may be provided alternatively or in addition to the aforementioned wash out channels 30, 30'. Also to be understood, channels 40, 40', 43, 43' are in fluid communication with the central opening 32 and the clearance 31, thus allowing for a net washout flow in the same manner described above.

Preferred embodiments are described in the following paragraphs:

1. A blood pump 1, comprising:
a pump casing 2 having a blood flow inlet 5 and a blood flow outlet 6 connected by a passage 7,
an impeller 3 arranged in said pump casing 2 so as to be rotatable about an axis of rotation 9, the impeller 2 being provided with blades 4 sized and shaped for conveying blood along the passage 7 from the blood flow inlet 5 to the blood flow outlet 6, the impeller 3 being rotatably supported in the pump casing 2 by at least one bearing 10, 20,
wherein a surface of the impeller 3 faces a surface of the pump casing 2 spaced from said surface of the impeller 3 by a clearance 31, the clearance 31 being in fluid connection with the passage 7 at a clearance transition point 36,
wherein at least one wash out channel 30 extends through the impeller 3 and is in fluid connection with the passage 7 via a first opening 34 and with the clearance 31 via a second opening 35,
wherein the first opening 34 of the wash out channel 30 is arranged in an area of the impeller 3 that—during operation of the blood pump 1—is under a higher pressure than the clearance transition point 36 so as to cause a blood flow from the first opening 34 through the wash out channel 30 and the clearance 31 to the clearance transition point 36.

2. The blood pump of paragraph 1, wherein the first opening 34 of the wash out channel 30 is disposed in a downstream half of the impeller 3.

3. The blood pump of paragraph 1 or 2, wherein the first opening 34 of the wash out channel 30 is disposed in an area of the impeller 3 where—during operation of the blood pump 1—the pressure is higher than a median pressure with respect to a pressure distribution along a length of the passage 7 where the impeller 3 is situated.

4. The blood pump of any one of paragraphs 1 to 3, wherein the first opening 34 of the wash out channel 30 is disposed in an area of the impeller 3 where—during operation of the blood pump 1—the pressure is substantially the maximum pressure with respect to a pressure distribution along a length of the passage 7 where the impeller 3 is situated.

5. The blood pump of any one of paragraphs 1 to 4, wherein the blood flow from the first opening 34 through the wash out channel 30 and the clearance 31 to the clearance transition point 36 is in a direction towards the blood flow outlet 6 of the pump casing 2.

6. The blood pump of any one of paragraphs 1 to 5, wherein the impeller 3 has a portion 33 in a downstream direction extending radially outward, the first opening 34 of the wash out channel 30 being disposed in said portion 33.

7. The blood pump of paragraph 6, wherein said portion 33 conically tapers radially outward in a downstream direction.

8. The blood pump of paragraph 6 or 7, wherein the blades 4 of the impeller 3 extend over said portion 33.

9. The blood pump of any one of paragraphs 6 to 8, wherein the portion 33 is integrally formed with the impeller 3 or separately formed.

10. The blood pump of any one of paragraphs 1 to 8, wherein the wash out channel 33 is operatively associated with a secondary pump for pumping blood from the first opening 34 through the wash out channel 30 towards the clearance transition point 36, wherein the secondary pump is formed at least partially by said at least one wash out channel 30 extending through the impeller 3 along a direction having at least one tangential directional component.

11. The blood pump of any one of paragraphs 1 to 10, wherein the wash out channel 30 extends linearly through the impeller 3 and is offset relative to the axis of rotation 9.

12. The blood pump of paragraph 11, wherein the wash out channel 30 extends in a plane that is parallel to the axis of rotation 9.

13. The blood pump of any one of paragraphs 1 to 10, wherein the wash out channel 30 is curved and extends from the first opening 34 in a direction around the axis of rotation 9.

14. The blood pump of any one of paragraphs 1 to 13, wherein the wash out channel 30 extends from the first opening 34 at an angle relative to a surface of the impeller 3 in a circumferential direction opposite the direction of rotation.

15. The blood pump of paragraph 14, wherein the angle is less than 20°, preferably less than 15°, more preferably less than 10°.

16. The blood pump of paragraph 14 or 15, wherein the wash out channel 30 extends from the first opening 34 in a substantially tangential direction relative to a surface of the impeller 3.

17. The blood pump of any one of paragraphs 1 to 16, wherein a distance between the second opening 35 and the axis of rotation 9 is less than or equal to a distance between the first opening 34 and the axis of rotation 9.

18. The blood pump of any one of paragraphs 1 to 17, wherein a distance between the axis of rotation 9 and the first opening 34 is less than 50%, preferably less than 40%, more preferably less than 30% of a distance between the axis of rotation 9 and the clearance transition point 36.

19. The blood pump of any one of paragraphs 1 to 18, wherein the impeller 3 comprises a central opening 32 extending along the axis of rotation 9 and at least partially accommodating the bearing 20, wherein the second opening 35 is in fluid connection with the central opening 32.

20. The blood pump of any one of paragraphs 1 to 19, wherein the wash out channel 30 at the second opening 35 is directed towards the axis of rotation 9 substantially in a radial direction.

21. The blood pump of any one of paragraphs 1 to 20, wherein the first opening 34 of the wash out channel 30 is disposed adjacent to one of the blades 4 of the impeller 3 on a forward side of the blade 4 with respect to the direction of rotation.

22. The blood pump of any one of paragraphs 1 to 21, wherein a cross section of the first opening 34 is circular.

23. The blood pump of any one of paragraphs 1 to 21, wherein a cross section of the first opening 34 is non-circular.

24. The blood pump of any one of paragraphs 1 to 23, wherein the first opening 34 is formed by an end portion of the wash out channel 30 that is at least partially exposed due to an incline of the wash out channel 30 relative to a surface of the impeller 3.

25. The blood pump of any one of paragraphs 1 to 24, wherein a protrusion 38 extends into the first opening 34 of the wash out channel 30 and is sized and shaped to increase a blood flow through the first opening 34 into the wash out channel 30.

26. The blood pump of any one of paragraphs 1 to 25, wherein the impeller 3 comprises at least one wing 39 extending radially therefrom and being disposed adjacent to and behind the first opening 34 of the wash out channel 30 with respect to the direction of rotation.

27. The blood pump of paragraph 26, wherein the wing 39 extends over the first opening 34 of the wash out channel 30 and opens in the direction of rotation so as to allow blood to enter the first opening 34.

28. The blood pump of any one of paragraphs 1 to 25, wherein the impeller 3 comprises a protrusion extending radially therefrom, the protrusion comprising the first opening 34 such that a cross section of the first opening 34 extends at an angle relative to the surface of the impeller 3 and opens in the direction of rotation, wherein the angle preferably is greater than 45°, more preferably 90°.

29. The blood pump of any one of paragraphs 1 to 28 comprising two or more wash out channels 30 that are symmetrically arranged with respect to the axis of rotation 9.

30. The blood pump of paragraph 10 and any one of paragraphs 1 to 9 and 11 to 29, wherein the secondary pump comprises grooves or blades formed in a surface of the impeller 3.

31. The blood pump of any one of paragraphs 1 to 30, wherein the first opening 41 is disposed on a forward side of the blade 4, and the second opening 42 is disposed on a backward side of the blade 4, and the wash out channel 40 extends underneath the blade 4.

32. The blood pump of any one of paragraphs 1 to 31, wherein the wash out channel 43 extends within the blade 4, wherein the first opening 44 is disposed on a forward side of the blade 4 and the second opening 45 is disposed in the blade 4, preferably on a radially outer edge of the blade 4.

33. The blood pump of any one of paragraphs 1 to 32, wherein the bearing 20 is a pivot bearing.

34. The blood pump of any one of paragraphs 1 to 33, wherein the pump 1 is an axial blood pump, a centrifugal blood pump or a mixed-type blood pump.

The invention claimed is:

1. A blood pump, comprising:
    a pump casing having a blood flow inlet and a blood flow outlet connected by a passage,
    an impeller arranged in said pump casing so as to be rotatable about an axis of rotation, the impeller being provided with at least one blade sized and shaped for conveying blood along the passage from the blood flow inlet to the blood flow outlet, the impeller being rotatably supported in the pump casing by at least one bearing,
    wherein a surface of the impeller faces a surface of the pump casing spaced from said surface of the impeller by a clearance, the clearance being in fluid connection with the passage at a clearance transition point at a downstream side of the impeller,
    wherein at least one wash out channel extends through the impeller and is in fluid connection with the passage via a first opening and with the clearance via a second opening,
    wherein the first opening of the wash out channel is disposed adjacent to the at least one blade of the impeller on a forward side of the at least one blade with respect to a direction of rotation such that during operation of the blood pump the first opening of the wash out channel is under a pressure that is higher than a pressure at the clearance transition point so as to cause a blood flow from the first opening through the wash out channel and the clearance to the clearance transition point.

2. The blood pump of claim 1, wherein the first opening of the wash out channel is disposed in a downstream half of the impeller.

3. The blood pump of claim 1, wherein during operation of the blood pump, the pressure of an area of the impeller where the first opening of the wash out channel is arranged is higher than a median pressure with respect to a pressure distribution along a length of the passage where the impeller is situated.

4. The blood pump of claim 3, wherein during operation of the blood pump, the pressure of the area of the impeller where the first opening of the wash out channel is arranged is a maximum pressure with respect to the pressure distribution along the length of the passage where the impeller is situated.

5. The blood pump of claim 1, Wherein the blood flow from the first opening through the wash out channel and the clearance to the clearance transition point is in a direction towards the blood flow outlet of the pump casing.

6. The blood pump of claim 1, wherein the impeller has a portion in a downstream direction extending radially outward, the first opening of the wash out channel being disposed in said portion.

7. The blood pump of claim 1, wherein the wash out channel is operatively associated with a secondary pump for pumping blood from the first opening through the wash out channel towards the clearance transition point, wherein the secondary pump is formed at least partially by said at least one wash out channel extending through the impeller along a direction having at least one tangential directional component.

8. The blood pump of claim 1, wherein the wash out channel extends linearly through the impeller and is offset relative to the axis of rotation.

9. The blood pump of claim 8, wherein the wash out channel extends in a plane that is parallel to the axis of rotation.

10. The blood pump of claim 1, wherein the wash out channel is curved and extends from the first opening in a direction around the axis of rotation.

11. The blood pump of claim 1, wherein the wash out channel extends from the first opening at an angle relative to the surface of the impeller in a circumferential direction opposite a direction of rotation, wherein the angle is less than 20°.

12. The blood pump of claim 11, wherein the angle is less than 15°.

13. The blood pump of claim 12, wherein the angle is less than 10°.

14. The blood pump of claim 1, wherein the impeller comprises a central opening extending along the axis of rotation and at least partially accommodating the bearing, wherein the second opening is in fluid connection with the central opening.

15. The blood pump of claim 1, wherein the wash out channel at the second opening is directed towards the axis of rotation substantially in a radial direction, wherein a distance between the axis of rotation and the first opening is less than 50% of a distance between the axis of rotation and the clearance transition point.

16. The blood pump of claim 15, wherein the distance between the axis of rotation and the first opening is less than 40% of the distance between the axis of rotation and the clearance transition point.

17. The blood pump of claim 16, wherein the distance between the axis of rotation and the first opening is less than 30% of the distance between the axis of rotation and the clearance transition point.

18. The blood pump of claim 1, wherein a cross section of the first opening is circular or non-circular.

19. The blood pump of claim 1, wherein the first opening is formed by an end portion of the wash out channel that is at least partially exposed due to an incline of the wash out channel relative to the surface of the impeller.

20. The blood pump of claim 1, Wherein a protrusion extends into the first opening of the wash out channel and is sized and shaped to increase blood flow through the first opening into the wash out channel, wherein the impeller comprises at least one wing extending radially therefrom and being disposed adjacent to and behind the first opening of the wash out channel with respect to a direction of rotation.

21. The blood pump of claim 20, wherein the at least one wing extends over the first opening of the wash out channel and opens in the direction of rotation so as to allow blood to enter the first opening.

* * * * *

UNITED STATES PATENT AND TRADEMARK OFFICE
CERTIFICATE OF CORRECTION

| | |
|---|---|
| PATENT NO. | : 11,103,689 B2 |
| APPLICATION NO. | : 15/556639 |
| DATED | : August 31, 2021 |
| INVENTOR(S) | : Thorsten Siess et al. |

It is certified that error appears in the above-identified patent and that said Letters Patent is hereby corrected as shown below:

In the Specification

Column 11, Line 55:
Now reads: "2"; should read -- 3 --

In the Claims

Column 14, Claim 5, Line 56:
Now reads: "Wherein"; should read -- wherein --

Column 16, Claim 20, Line 18:
Now reads: "Wherein"; should read -- wherein --

Signed and Sealed this
Fifth Day of July, 2022

Katherine Kelly Vidal
*Director of the United States Patent and Trademark Office*